United States Patent
Kassab et al.

(10) Patent No.: US 11,633,100 B2
(45) Date of Patent: Apr. 25, 2023

(54) STROKE, CONCUSSION, AND COGNITIVE DYSFUNCTION DIAGNOSTIC METHOD AND DEVICE

(71) Applicants: Ghassan S. Kassab, La Jolla, CA (US); Ali Dabiri, San Diego, CA (US)

(72) Inventors: Ghassan S. Kassab, La Jolla, CA (US); Ali Dabiri, San Diego, CA (US)

(73) Assignee: 3DT Holdings, LLC, San Diego, CA (US)

( * ) Notice: Subject to any disclaimer, the term of this patent is extended or adjusted under 35 U.S.C. 154(b) by 924 days.

(21) Appl. No.: 16/391,614

(22) Filed: Apr. 23, 2019

(65) Prior Publication Data
US 2019/0320896 A1 Oct. 24, 2019

Related U.S. Application Data

(60) Provisional application No. 62/673,192, filed on May 18, 2018, provisional application No. 62/661,284, filed on Apr. 23, 2018.

(51) Int. Cl.
*A61B 3/12* (2006.01)
*A61B 5/00* (2006.01)

(52) U.S. Cl.
CPC .......... *A61B 3/1241* (2013.01); *A61B 5/0071* (2013.01); *A61B 5/4064* (2013.01); *A61B 5/4088* (2013.01)

(58) Field of Classification Search
CPC ....... A61B 3/1241; A61B 3/10; A61B 5/0071; A61B 5/4064; A61B 5/4088; A61B 5/0082; A61K 49/0021; A61K 49/0043
See application file for complete search history.

(56) References Cited

U.S. PATENT DOCUMENTS

| | | | | |
|---|---|---|---|---|
| 5,225,859 A | * | 7/1993 | Fleischman | A61B 3/145 351/221 |
| 5,377,686 A | * | 1/1995 | O'Rourke | A61B 3/14 607/93 |
| 2013/0128227 A1 | * | 5/2013 | Cui | A61B 3/10 351/246 |
| 2016/0000324 A1 | * | 1/2016 | Rege | A61B 3/1208 600/479 |
| 2017/0367598 A1 | * | 12/2017 | Madsen | A61B 5/02416 |

FOREIGN PATENT DOCUMENTS

WO    WO-2015188142 A1 * 12/2015 ............... A61B 3/00

OTHER PUBLICATIONS

Hitomi, Emi, et al. "Blood-ocular barrier disruption in patients with acute stroke." Neurology 90.11 (2018): e915-e923. (Year: 2018).*

(Continued)

*Primary Examiner* — Sean D Mattson (57) ABSTRACT

A method of detecting injury to the brain such as stroke, concussion and cognitive dysfunction using a contrast agent and light source. The blood ocular barrier is disrupted when said injury occurs, allowing the entry of contrast agent into the aqueous and vitreous humor. An exemplary method comprises injecting a contrast agent into a peripheral location and then testing for leakage of contrast agent into the eye cavity by observing for light reflection, when a beam of light incidents on the contrast agent in the eye.

6 Claims, 4 Drawing Sheets

(56) References Cited

OTHER PUBLICATIONS

Liu, Yanlan, et al. "Fluorescence-enhanced gadolinium-doped zinc oxide quantum dots for magnetic resonance and fluorescence imaging." Biomaterials 32.4 (2011): 1185-1192. (Year: 2011).*

Kuo, Tsungrong, et al. "AS1411 aptamer-conjugated Gd2O3: Eu nanoparticles for target-specific computed tomography/magnetic resonance/fluorescence molecular imaging." Nano research 7.5 (2014): 658-669. (Year: 2014).*

* cited by examiner

STROKE, CONCUSSION, AND COGNITIVE DYSFUNCTION DIAGNOSTIC METHOD AND DEVICE

PRIORITY AND RELATED APPLICATIONS

The present patent application relates to, and claims the priority benefit of, U.S. Provisional Patent Application Ser. No. 62/661,284, filed on Apr. 23, 2018, the contents of which are hereby incorporated by reference in their entirety into this disclosure.

The present patent application is also related to, and claims the priority benefit of, U.S. Provisional Patent Application Ser. No. 62/673,192, filed on May 18, 2018, the contents of which are hereby incorporated by reference in their entirety into this disclosure.

BACKGROUND

A stroke is a medical emergency that occurs when blood supply to the brain is interrupted. This results in the death of neurons causing permanent damage to the brain and potentially death. A large number of people suffer stroke worldwide (15 million each year). Stroke affects 7 million Americans with ~800,000 new cases occurring each year. In the U.S., stroke is the fourth leading cause of death after heart disease, cancer, and chronic lower respiratory disease. Also, stroke is the leading cause of long-term disability which leads to diminished patient quality of life (QOL) with large accompanying healthcare costs (~$34 billion/year). Stroke-related costs and deaths are expected to rise with ever increasing aging population. Incidences of stroke are expected to more than double over the next 40 years.

The prevalence of stroke in the US is seen most prominently in women and minorities, such as African Americans, and the increasing elderly population. Multiple factors contribute to stroke incidences including: cardiac rhythm disorders (e.g., atrial fibrillation (AF) ~2-6 million U.S. currently), diabetes mellitus (18-23 million), high cholesterol and/or blood pressure (76-103 million), tobacco usage (70 million), end-stage renal disease (0.5 million), and physical inactivity (102 million). Stroke prevention is difficult to achieve because certain factors, such as tobacco usage and physical activity, are out of clinical control, while other factors, like AF, although treatable with therapies such as antiarrhythmics, cardioversion, or ablation, have failed to show a significant decrease in stroke occurrence. In addition, recent transcatheter procedures such as transcatheter aortic valve implants may increase the risk of stroke.

Approximately 85% of strokes are ischemic in nature and result from thromboembolic occlusion of a major cerebral artery or its branches. Intracranial atherosclerosis is one of the most common causes of ischemic stroke worldwide and is associated with a high rate of recurrence. Transient ischemic attacks (TIAs) cause similar symptoms, but the blockage of blood flow to the brain is temporary. About one-third of people who have a TIA will have a stroke within one year. Chronic ischemia may result in a form of dementia called vascular dementia. It can cause damage to the white matter, but it does not seem to be associated with the BBB breakdown in short term. Sub-clinical or silent stroke is a stroke that does not have any outward symptoms associated with the stroke and the patient is typically unaware they have suffered a stroke. In a broad study in 1998, about 11 million people were estimated to have experienced silent stroke. The silent strokes typically cause brain lesions, but it is doubtful that they will be associated with the BBB disruption.

The most commonly used imaging techniques to assess intracranial atherosclerosis, such as computed tomographic angiography or magnetic resonance angiography, provide information on the degree of narrowing of the vascular lumen. Most classification schemes for ischemic stroke etiology require plaque to cause ≥50% stenosis for a given stroke to be attributable to large-artery atherosclerosis. MRI studies of the extracranial carotid arteries, however, suggest that many atherosclerotic plaques have high-risk features despite the absence of significant luminal narrowing. It is unknown to what extent similar non-stenotic intracranial atherosclerotic plaque may be responsible for a proportion of the approximately 1 in 3 ischemic strokes for which no clear etiology can be determined.

Recent investigations have begun to address this problem by leveraging high-resolution, multiplanar MRI to detect high risk abnormalities of the intracranial vessel walls. Previous studies in both the coronary and extracranial carotid arteries have shown that abnormal plaque enhancement after the administration of gadolinium contrast agent is a marker of inflammation, neovascularity, and plaque instability. For this reason, plaque enhancement has been recently studied as a potential high-risk plaque feature in the intracranial circulation. Plaque enhancement is a particularly attractive MRI biomarker because it can be rapidly detected, qualitatively assessed, and does not require significant image postprocessing to analyze. A systematic review and meta-analysis to evaluate the association between abnormal plaque enhancement on high-resolution MRI and acute ischemic stroke has been performed. The result indicates that intracranial plaque enhancement on high-resolution vessel wall MRI is strongly associated with ischemic stroke. It is concluded that evaluation for plaque enhancement on MRI may be a useful test to improve diagnostic yield in patients with ischemic strokes of undetermined etiology.

One of the minimally-invasive diagnosis of the cerebral ischemia is the gadolinium enhanced MM imaging. It is mainly used in patients to detect brain tissue damaged by an ischemic stroke and brain hemorrhage. Cerebral angiogram is also used to provide detailed view of the arteries in the brain and the neck. Although advances in modern CTA and MM imaging allow, in majority of cases, for sufficient information without the need for cerebral angiogram, but in some cases an angiogram is requested due to lack of sufficient information with MM. These techniques are expensive and, in the case of angiography, include risk of x-ray exposure.

Although MRI remains valuable in the investigation and management of ischemic stroke, it has been found that certain stroke syndromes are more commonly associated with diffusion-weighted imaging (DWI)-negative MRI. This case series identifies 16 cases of DWI-negative stroke, constituting 2.3% of ischemic stroke patients who had MRI. They classified almost all cases as either posterior circulation or lacunar stroke, with isolated internuclear ophthalmoplegia and ataxic hemiparesis being the most common syndromes.

In the absence of blood brain barrier (BBB) disruption, gadolinium contrast given during MRI remains in the intravascular compartment and does not enter brain parenchyma or cerebrospinal fluid (CSF). When gadolinium leaks into brain parenchyma, it can be detected with dynamic susceptibility contrast imaging. Disruption of the BBB can occur in acute and chronic cerebral ischemia and gadolinium can leak into the CSF Like BBB disruption, the integrity of blood-ocular barrier (BOB) can be affected by vascular disease. gadolinium leaks into ocular structures (GLOS) have been reported in the setting of central retinal artery occlusion and kidney disease and may therefore be a marker for disruption of the BOB. A method that can accurately detect the presence of gadolinium in the eye would provide a powerful tool for point of care stroke diagnostic that would allow earlier intervention in order to minimize the stroke injury. Concussion is now recognized as a major health issue, with many millions of cases reported worldwide each year. Indeed, although alternatively referred to as mild traumatic brain injury (mTBI), for many there is nothing 'mild' about concussion, with approximately 15% of patients suffering persisting neurocognitive dysfunction. Moreover, an increasing number of reports link exposure to repetitive concussions with progressive neurodegeneration, including 'chronic traumatic encephalopathy' (CTE). Despite growing public alarm regarding the aftermath of concussion, there remains no consensus on the underlying pathophysiology of the injury. In part, this is due to the limited availability of human post-mortem brain tissue for examination from this typically non-lethal injury. As such, concussion remains in part defined by an absence of the overt brain pathologies characteristic of higher levels of TBI, including, hematoma, contusion or marked brain swelling. However, emerging experimental and clinical data indicates that concussion may share one of the most consistently observed pathologies of moderate and severe TBI, diffuse axonal injury (DAI).

Studies indicate that DAI is a key pathological substrate of concussion in humans due to mechanical vulnerability of white matter axons. Nonetheless, these findings do not preclude the possibility that other brain structures also suffer mechanical damage within and beyond white matter. While the resulting pathological effects of BBB dysfunction remain to be determined in single concussion, BBB permeability along with perivascular neuropathologies including neurofibrillary and glial tauopathy have been reported in individuals with CTE following exposure to repetitive concussion. Recent data suggest that BBB disruption represents a new and important pathological feature of concussion. We assume similar to stroke, that the integrity of the BOB can also be affected following the BBB disruption aftermath of concussion.

Vascular contributions to cognitive impairment are increasingly recognized. Moreover, small vessel disease of the brain has been estimated to contribute to approximately 50% of all dementias worldwide, including those caused by Alzheimer's disease (AD). Vascular changes in AD have been typically attributed to the vasoactive and/or vasculotoxic effects of amyloid-β (Aβ) and more recently tau. Animal studies suggest that Aβ and tau lead to blood vessel abnormalities and blood-brain barrier (BBB) breakdown. Although neurovascular dysfunction and BBB breakdown develop early in AD, how they relate to changes in the AD classical biomarkers Aβ and tau, which also develop before dementia remains unknown. The data show that individuals with early cognitive dysfunction develop brain capillary damage and BBB breakdown in the hippocampus irrespective of Alzheimer's Aβ and/or tau biomarker changes, suggesting that BBB breakdown is an early biomarker of cognitive dysfunction (CD) independent of Aβ and tau.

BRIEF SUMMARY

The present method and associated device can be used to detect the acute stroke and transient ischemic attack (TIA) through the detection of contrast agent in the aqueous chamber of the eye by intravenous (i.v.) injection. It is expected that there will not be any contrast agent in the eye for TIA cases due to the lack of BBB disruption. The present method and associated device can also be used to detect concussion and CD. These diagnostic tests can be performed in outpatient setting that does not require MRI facility.

The objective of this invention is to minimally-invasive detect stroke/concussion/CD, through the detection of gadolinium in the eye by intravenous (IV) injection of contrast agent. The agent is safe as it is used routinely in MRI imaging. Gadolinium-DTPA, one of the commercial contrast agents, has UV absorption spectra. The UV radiation at this wavelength is safe for short period of time. The UV detectors prices are very affordable for any medical clinic. The rationale for this proposal is the detection of gadolinium in the eye can be made much more readily and inexpensively than with an MRI image of the brain.

The eventual feature of the device will be portability and simplicity of its operation that can be used by a medical technician in medical office, emergency outfits, in ambulances and in remote regions.

It is also possible to use commercially available sodium fluorescein (SF) rather than gadolinium due to its very high absorption coefficient in the visible spectrum. Although commonly referred to as fluorescein, the dye used for fluorescein angiography is actually sodium fluorescein, the water-soluble salt ($C_{20}H_{10}Na_2O_5$). Fluorescein angiography is performed by injecting sodium fluorescein dye as a bolus into a peripheral vein. Upon entering the circulation, approximately 80% of the dye molecules bind to plasma proteins, which significantly reduces fluorescence because the free electrons that form this chemical bond are subsequently unavailable for excitation. The remaining unbound or free fluorescein molecules fluoresce in the green light range when excited with light of the appropriate wavelength. With a molecular weight of 376, fluorescein diffuses freely out of all capillaries except those of the central nervous system, including the retina. The dye is metabolized by the kidneys and is eliminated through the urine within 24 to 36 hours of administration. In a typical fluorescein angiography, about twelve seconds after the injection, the dye appears in the arteries of the retina. Over a two to five seconds period, the dye travels through the very small vessels and fills the veins. Ten minutes after injection, the dye mostly evacuated from the eye. In the case of stroke as discussed above, it takes longer (1-2 hour) to be able to observe the contrast agent in the eye that has diffused to the aqueous chamber through the BBB and blood aqueous barrier (BAB) rupture and consequently there would not be any contrast agent left in the vascular system of the eye before the sodium fluorescein appears in the aqueous chamber resulting from the barriers rupture. This would provide us with an isolated signal associated with possible ischemic stroke/concussion and CD.

An exemplary method includes the steps of: 1) administering gadolinium/SF; and 2) determining the presence or absence of gadolinium/SF in the patient's eye; and 3) diagnosing the potential for stroke/concussion/CD based on the presence of gadolinium/SF.

An exemplary method of detecting contrast agent in the eye comprises the steps of: injecting a contrast agent; incidenting a light into the eye wherein the light is reactive with the contrast agent; and detecting the light returning from the eye.

In an exemplary method of detecting contrast agent in the eye, the contrast agent is injected at a location other than the eye.

In an exemplary method of detecting contrast agent in the eye, the light returning from the eye is less intense than the light incident into the eye.

In an exemplary method of detecting contrast agent in the eye, the contrast agent comprises gadolinium/SF. In an exemplary method of detecting contrast agent in the eye, the method also comprises the step of waiting a period of time after injecting the contrast agent.

In an exemplary method of detecting contrast agent in the eye, the steps of incidenting a light into the eye and detecting the returning light are performed using a UV emission and detection device for gadolinium and using fluorescence light and detection device for SF.

In an exemplary method of detecting gadolinium in the eye, the incident light is ultraviolet light. In an exemplary method of detecting SF in the eye the incidenting light is visible.

In an exemplary method of detecting contrast agent in the eye, the light is incident into the anterior chamber of the eye. In an exemplary method of detecting contrast agent in the eye detecting device detects light reflected from the anterior chamber.

Both contrast agents are safe as it is used routinely in MRI imaging and fluorescein angiography by ophthalmologists. The UV radiation at the desired wavelength is safe for short period of time. The UV detectors and angiography cameras are commercially available and very cost effective for any medical clinic. This innovation would allow point of care (POC) diagnostic that does not require an MRI or angiography (invasive procedure) at specialized clinics. This innovation may also reduce false positives and only recommend MRI for further therapy related diagnosis.

The present disclosure includes disclosure of a method of detecting stroke/concussion/cognitive dysfunction through the detection of contrast agent in the eye comprising the steps of injecting a contrast agent into a peripheral vessel; incidenting or exciting a light into the eye wherein the light emits from the contrast agent; and detecting the light returning from the eye.

The present disclosure includes disclosure of a method wherein the contrast agent is injected at a location other than the eye.

The present disclosure includes disclosure of a method wherein the contrast agent comprises gadolinium or sodium fluorescein or other biocompatible contrast agent.

The present disclosure includes disclosure of a method further comprising the step of waiting a period of time after contrast agent injection.

The present disclosure includes disclosure of a method wherein the steps of incidenting or exciting light into the eye and detecting the returning light are performed using a UV emission for gadolinium and fluorescence signal for sodium fluorescein, via a detection device.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The objective of the present invention is to minimally invasive detect stroke, concussion and cognitive dysfunction, through the detection of gadolinium or sodium fluorescein in the eye by IV injection of contrast agent. Gadolinium is safe and it is used routinely in MRI imaging. Gadolinium-DTPA, one of the commercial contrast agents, has UV absorption spectra. The UV radiation at this wavelength is safe for relatively short periods of time. The UV detector cost is very affordable for any medical clinic.

The sodium fluorescein is safe and it is routinely used in fluorescein angiography. The sodium fluorescein has high absorption coefficient in the visible spectrum. The angiography camera cost is very affordable for any medical clinic. The smartphone fundus camera is commercially available.

The major innovation of this method is to leverage the eye as the window to the brain. A safe and effective device that can substantially reduce the cost of stroke/concussion and cognitive dysfunction diagnosis without MRI imaging would have a far-reaching impact on the healthcare system and associated costs. The eventual feature of the device will be portability and simplicity of its operation that can be used by a medical technician in medical office, emergency outfits, in ambulances and in remote regions.

A recent study of acute stroke patients showed gadolinium leakage into ocular structures (GLOS) during MRI imaging with gadolinium administration. The results indicate that at 2 hours after administration of the contrast agent, GLOS was more common in the aqueous chamber alone, occurring in 67% of patients, compared to the vitreous chamber alone, seen in 6% of patients with increasing amount in 24 hours after the administration. This could be due to disruption of blood-ocular barrier (BOB) like the disruption of blood-brain barrier (BBB) in acute and chronic stroke. Detection of such conditions in the eye can tremendously reduce the cost of the health care by elimination of MRI imaging.

Aqueous humor is a clear fluid (98% water) that fills and helps form the anterior and posterior chambers of the eye.

Active secretion is thought to be the major contributor to aqueous formation, responsible for approximately 80% to 90% of the total aqueous humor formation. Active transport takes place through selective trans-cellular movement of anions, cations, and other molecules across a concentration gradient in blood-aqueous barrier. It is expected that other mechanisms in addition to the active transport are responsible for the transport of gadolinium to the aqueous humor when BOB is disrupted. The BOB is composed primarily of a blood-retinal barrier and a blood-aqueous barrier.

The vitreous chamber volume is more than an order of magnitude larger than vitreous humor. It is surrounded by and attached to the retina and lens of the eye. It is virtually acellular, highly hydrated extracellular gel matrix, composed of approximately 99% water. The vitreous does not undergo a regular formation and drainage process like the aqueous humor. Instead, it stays permanently in the vitreous body of the eye.

The rationale is that the detection of the contrast agent in the eye can be made much more readily (point of care) and inexpensively than with an MRI image of the brain.

Figure 1:
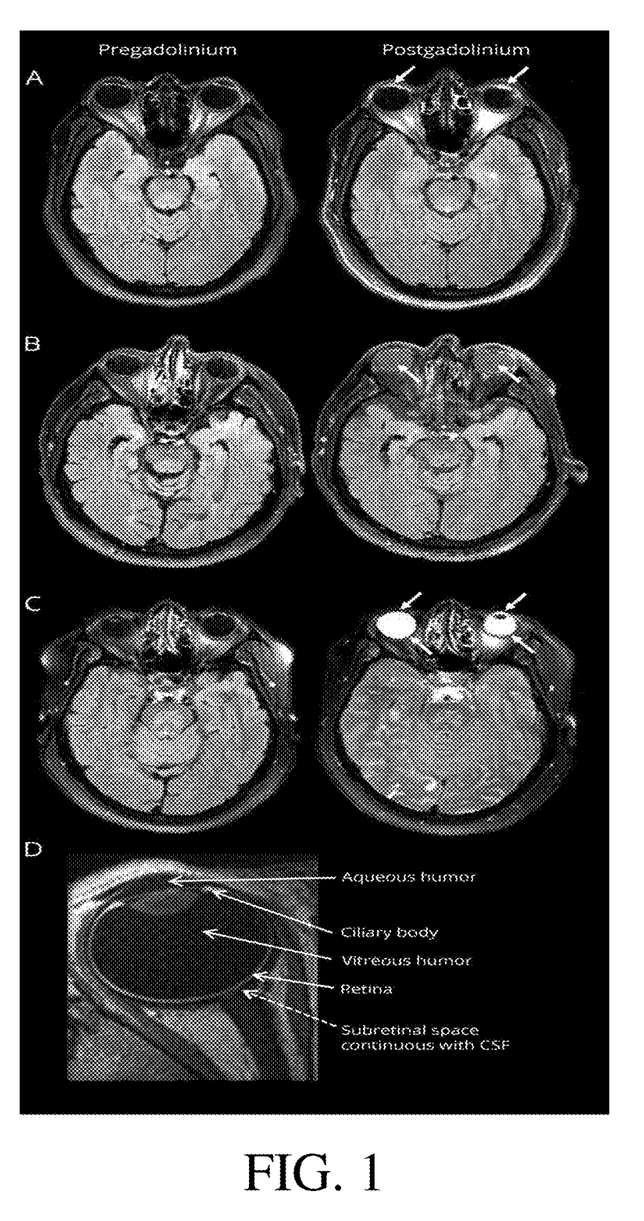
FIG. 1 shows pre- and post-gadolinium fluid-attenuated inversion recovery MRI images are shown for patients demonstrating GLOS of the aqueous chamber (subsection A, indicated by arrows), the vitreous chamber (subsection B, indicated by arrows), rapid diffuse GLOS (subsection C), and ocular structures (subsection D), according to exemplary embodiments of the present disclosure.

It is noted GLOS is a common finding in patients with acute stroke, prompting a retrospective study to determine its prevalence and assess its relationship to clinical and radiographic findings. A study of the frequency and nature of findings in 167 patients was performed. At 2 hours after administration of the contrast, GLOS was more common in the aqueous chamber alone, occurring in 67% of patients, compared to the vitreous chamber alone, seen in 6% of patients (subsection A of FIG. 1). GLOS occurred in both chambers in 27% of patients. At 24 hours, GLOS was present in 75% patients, always involving the vitreous chamber, but also affecting the aqueous chamber in 6% of cases (subsection B of FIG. 1). Patients with rapid diffusion of GLOS, defined as GLOS involving both chambers at 2 hours, had larger infarcts (p=0.022) and a higher degree of BBB permeability (p=0.025), (subsection C of FIG. 1). They concluded that GLOS is common in patients with acute stroke and delayed GLOS was a marker for chronic vascular disease. Subsection C of FIG. 1 shows an example of a rapid diffuse GLOS. The MRI image shows a high concentration of gadolinium-DTPA in the eye chamber cavity of patients with disrupted BOB, when injected with 0.1 mmol/kg of body weight.

Gadolinium Absorption Coefficient:

Improving the contrast in MRI requires contrast agents that are sufficiently stable and water-soluble with large values of molar relativity. It is commonly known that diethylenetriaminepentaacetic acid (DTPA) leads to the formation of highly stable complexes with trivalent lanthanide ions in aqueous solutions. Among the lanthanides, gadolinium (III) is preferred for in vivo MR applications because of its high paramagnetic character, and several Gd III complexes are in clinical use as they enhance the signal intensity to result in a positive contrast.

Figure 2:
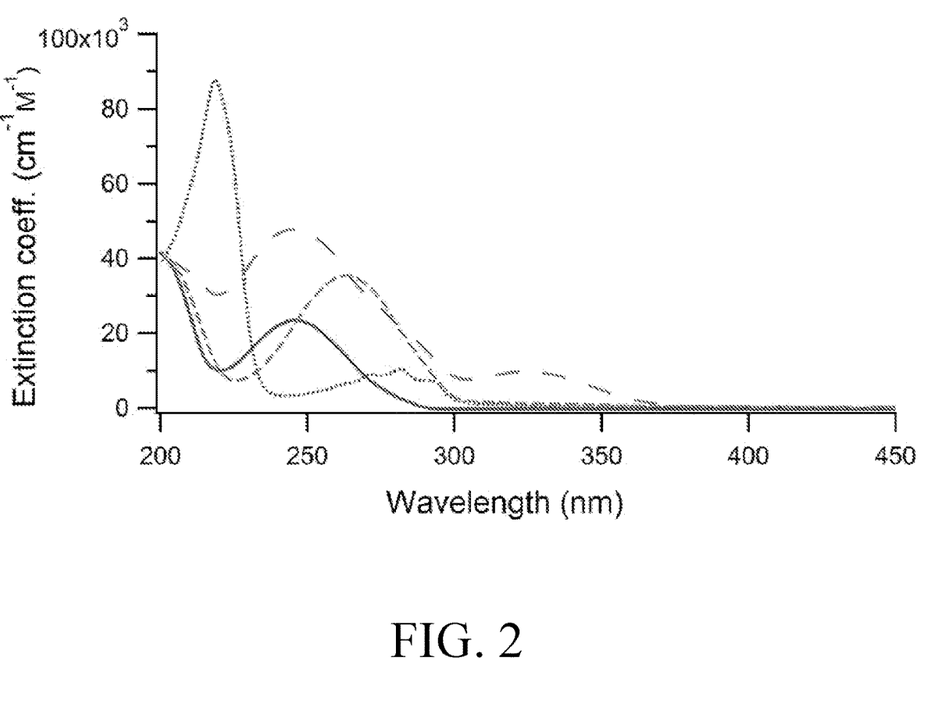
FIG. 2 shows a UV absorption spectra of gadolinium, according to an exemplary embodiment of the present disclosure.

All Gd III complexes displayed well-defined absorption bands as shown in FIG. 2. The absorption bands are all in the UV region. The peak absorption coefficient ranges from $20 \times 10^3$ to $90 \times 10^3$ cm$^{-1}$ M$^{-1}$. Most of the incident UV light stops at the lens and some will reflect to be measured in case of human since the human lens stops light with wavelength less than 300 nm. FIG. 2 shows UV/Vis absorption spectra of Gd-DTPA-BTolA (Gd1) (solid line), Gd-DTPA-BCoumA (Gd2) (long-dashed line), Gd-DTPA-BNaphA (Gd3) (dotted line) and Gd-DTPA-BEthA (Gd4) (short-dashed line) in water (pH=7.4, c=1×10−5 M). The Gd-DTPA-BCoumA is the preferred contrast agent to be used according to FIG. 2.

Sodium Fluorescein Absorption Coefficient

Figure 3:
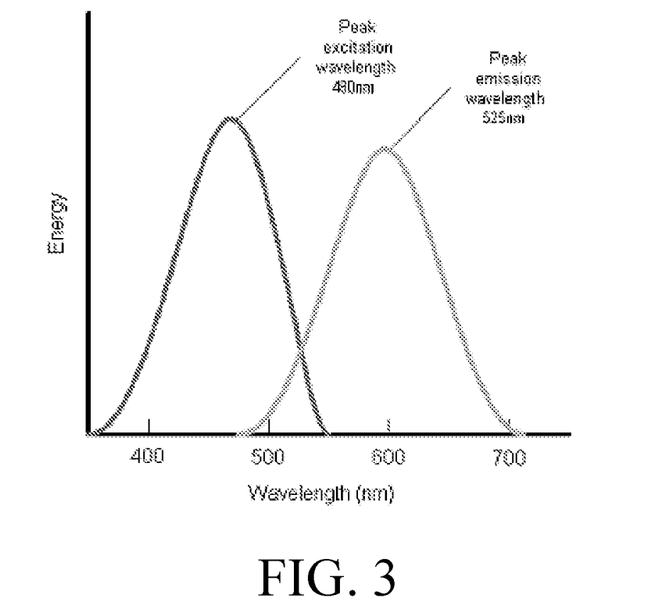
FIG. 3 shows visible absorption spectra for sodium fluorescein, according to an exemplary embodiment of the present disclosure.

Sodium fluorescein (SF) is another preferred contrast agent due to its very high absorption coefficient in the visible spectrum according to FIG. 3. Sodium fluorescein absorbs blue light, with peak excitation occurring at wavelengths between 465-490 nm (FIG. 3). The resulting fluorescence occurs at the yellow-green wavelengths of 520 to 535 nm. Fluorescence is detectable in concentrations between $10^{-1}$% and $10^{-7}$% due to its very high extinction coefficient. The extinction coefficient of fluorescein was estimated by the measuring the fluorescence emission spectrum of fluorescein dissolved in basic ethanol. The excitation wavelength was at 470 nm. The peak molar extinction coefficient was 92300 cm$^{-1}$M$^{-1}$ at 535 nm. In broad-spectrum illumination, diluted sodium fluorescein appears bright yellow-green in color. When illuminated with blue light, the yellow-green color intensifies dramatically. The camera will be the same as it is used for the eye fluorescein angiography.

Light Beam Path Length Estimate

MRI technology, with super-resolution, hyper-speed imaging and the integration of the thin-scanning layer, is applied to measure the 3-D biometric parameters of the eyeball. The volume of the human eyeball, anterior chamber, lens and the vitreous cavity is 6.0 ml, 0.35 ml, 0.18 ml, and 5.48 ml, respectively. The length of anterior-posterior diameter of the vitreous cavity is 16.0 mm. The ocular inner dimensions of horizontal, vertical and anterior-posterior planes were 22.5 mm, 23.3 mm and 22.6 mm, respectively. The length of the ocular axis is 23.1 mm. The light beam travels through the human eye cavity and reflected from the retina back to the detector. The emitted beams may travel through the cornea, lens and pupil into the posterior chamber. The total length is about 45 mm. There will not be any beam scattering since there is no cell inside the cavity to help the scattering of the photons. The length of the ocular axis is about 6.3 mm with the total beam path length of 12.5 mm.

For the gadolinium contrast agent the UV beam travels through the cornea and reflects from the lens back to the detector. The anterior chamber depth is about 3 mm. The UV beam path length is about 6 mm assuming that the UV light stops at the lens.

For the sodium fluorescein contrast agent, the blue light travels 22.6 mm through the lens and reaches the retina.

The last parameter to estimate is the concentration of the gadolinium inside the eye cavity to calculate the total absorbance through the Beer's law which is the product of absorption coefficient, the path length of the UV beam and the Gadolinium concentration inside the eye cavity.

Gadolinium Concentration Estimate

This method estimates the average concentration of the gadolinium in the human eye cavity and does not differentiate between the individual concentrations of aqueous humor and vitreous chamber. An order of magnitude estimate of the gadolinium concentration in the eye cavity is made in order to select a UV detector with an appropriate sensitivity. The estimate is made based on the value of the gadolinium injection used for the MRI imaging which is about 0.1 mmol/kg of the patient body mass. The gadolinium can diffuse into the vitreous chamber when the blood-retinal barrier is disrupted.

For humans, the gadolinium circulation is about $1.4 \times 10^{-3}$ mmol/per ml of circulating blood in a patient with a human body mass of 70 kg, assuming 5 liters of circulating blood. The gadolinium diffuses into the vitreous chamber when the blood-retinal barrier is disrupted. In the normal situation, the central retinal artery average diameter is about 417 μm with average arterial blood velocity of 3.47 cm/sec which results in average flow rate of 0.26 ml/min near the blood ocular barrier. We assume that 1% of the gadolinium content of the blood will diffuse in the vitreous chamber per minute which will be equal to $1.4 \times 10^{-3}$ mmol/ml$\times 0.26 \times 0.01$ ml/min=$3.7 \times 10^{-6}$ mmol/min gadolinium will be deposited in the chamber as time goes on and it reaches a value of $5 \times 10^{-3}$ mmol after 24 hours. This is about 0.07% of total gadolinium injection in 24 hours. Some of the gadolinium will be washed out since aqueous humor will undergo a regular formation and drainage process, unlike the vitreous chamber. The corresponding UV light absorbance in the human eye cavity will be about $3 \times 10^{-2}$ after 24 hours from Beer's law formula assuming extinction coefficient of $10 \times 10^{3}$ cm$^{-1}$ M$^{-1}$ according to FIG. 2 at 300 nm and 6 mm of beam path length.

Sodium Fluorescein Concentration Estimate

This method estimates the average absorbance of the sodium fluorescein in the human eye cavity and does not differentiate between the individual dye concentrations of aqueous humor and vitreous chamber. An order of magnitude estimate of the sodium fluorescein concentration in the eye cavity will be made to confirm acceptable imaging quality. The estimate will be made based on the value of the sodium fluorescein injection level. We will start with 500 mg of fluorescein which is a nominal value for fluorescein angiography for diagnosis and treatment of eye disorders, such as macular degeneration or diabetic retinopathy for human. This amount is present in 5 ml of 10% sodium fluorescein solution. We anticipate that the sodium fluorescein can diffuse into the aqueous chamber when the BBB and blood-aqueous barrier is disrupted. The concentration of sodium fluorescein in percent in the patient's vascular system is 5 ml/5000 ml=$10^{-1}$% with a human body mass of 70 kg, assuming 5 liters of circulating blood. A fraction of the contrast agent from the vascular system will flow through the BBB and BAB when they are disrupted. Even a very small fraction of $10^{-3}$ will translate into the contrast agent concentration of $10^{-4}$% in the aqueous chamber which is much larger than the level of detection (LOD) of angiography camera.

Exemplary Embodiment

Figure 4:
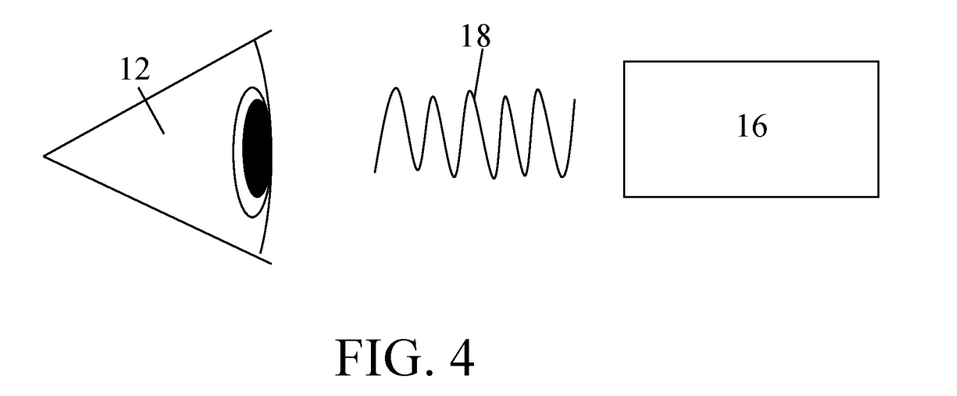
FIG. 4 shows a visual representation the system used.

In a preferred embodiment, the method comprises using a light incident and detection device 16 to detect presence or absence of intravenously injected contrast agent in an eye 12. As shown in FIG. 4, the light 18 is directed through the cornea towards the anterior chamber (in case of Gadolinium contrast agent) and retina (in case of sodium fluorescein contrast agent) of the eye 12. Light 18 will reflect from the lens/and or retina of the eye 12. As light 18 passes through the ocular structures the contrast agent will interfere with the light 18. The detector 16 analyzes the reflected light 18 informing the clinician about the presences or absence of contrast agent.

Figure 5:
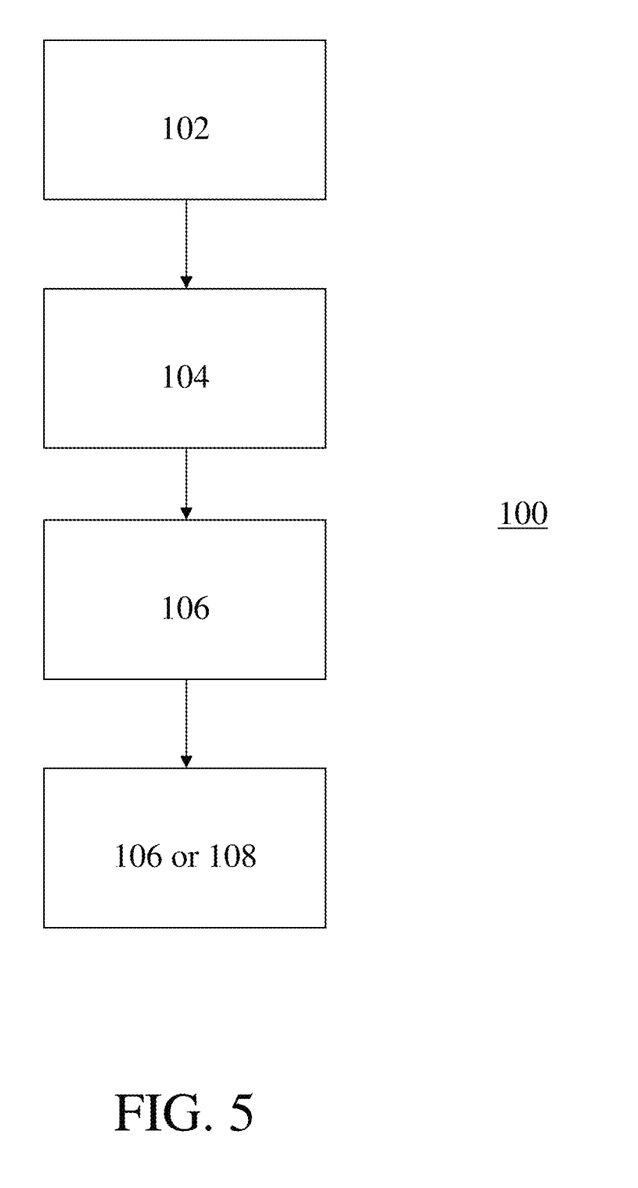
FIG. 5 shows a flowchart of the steps of an exemplary method.

The light incident (or excitation) and detection device 16 may be a UV spectrometer or similar device capable of sending UV light 18 of selected wavelengths and detecting the presence or absence of contrast agent. In another embodiment, the method uses light 18 in the visible spectrum for excitation and detection. The incident and detection device 16 can compare and determine the difference between the incident light and reflected light, such as by using a camera or other collector. That is, the device is capable of observing the effect of light passing in and out of the eye 12. In an embodiment, the UV wavelengths used will be in the 200-300 nm range. In a further embodiment, the sodium fluorescein contrast agent is reactive to light in the visible spectrum. In this embodiment the method directs light emitted in the visible spectrum into the patient's eye such as from a light incident and detection device. The contrast agent is preferably gadolinium-DPTA or sodium fluorescein, or may be any acceptable isotope or other compound or variation of gadolinium or fluorescein. Preferably, the contrast agent is biocompatible and reacts with light at a known wavelength. As shown in FIG. 5, the method 100 includes the step of intravenously injecting contrast agent into a patient to be diagnosed 102. The injection location may be a peripheral blood vessel. After contrast agent injection, the clinician may wait a period of time to pass before checking for contrast agent leakage into the ocular structures 104. That period of time may be 2 hours or longer. Either relatively shortly after injection of contrast agent or after waiting said period of time, the incident and detection device is activated 106. Light 18 is directed into the ocular structures of the patient's eye. The incident light 18 is reactive to the contrast agent and can be at least partly absorbed by the contrast agent and partly reflected back to the incident and detection device 106, or perhaps to an adjacent or similarly situated detection device 108. The patient can then be diagnosed and treated properly depending on the level of light absorption/reflected light.

In an exemplary embodiment, the emitted light 18 is directed to pass through the cornea and pupil and at the lens of the patient and the detector detects light reflecting from the lens.

In another embodiment, where visible light 18 is used, the visible light is directed into the patient's eye 12. The eye is observed for fluorescence to determine the presence of fluorescein and the patient may be diagnosed and treated based on the amount of fluorescence.

While various embodiments of devices for stroke, concussion, or cognitive dysfunction diagnostics and methods for the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method of diagnosing stroke/concussion/cognitive dysfunction in a patient through detection of a contrast agent in an eye of the patient comprising the steps of:
   injecting the contrast agent into a peripheral vessel of the patient;
   emitting a light into the eye of the patient, the light having a wavelength such that the light is absorbable by the contrast agent, wherein the light passes through an anterior chamber and/or a vitreous chamber of the eye where the light will be at least partially absorbed by the contrast agent present in the anterior chamber and/or the vitreous chamber of the eye, and a remainder of the light that is not absorbed by the contrast agent is reflected from the eye;

detecting the remainder of the light reflected from the eye;

detecting a presence or an absence of the contrast agent in the anterior chamber and/or the vitreous chamber of the eye by determining a difference between the remainder of the light reflected by the eye and the light emitted into the eye, wherein when the remainder of the light reflected by the eye is less than the light emitted into the eye indicates the presence of contrast agent in the anterior chamber and/or the vitreous chamber of the eye;

diagnosing stroke/concussion/cognitive dysfunction based on the presence of the contrast agent in the anterior chamber and/or the vitreous chamber of the eye; and wherein the contrast agent comprises gadolinium.

2. The method of claim 1, wherein the contrast agent is injected at a location other than the eye.

3. The method of claim 1, wherein the steps of emitting a light into the eye and detecting the remainder of the light reflected from the eye are performed using an ultraviolet (UV) emission and a detection device.

4. The method of claim 3, wherein the wavelength of the light is between 200-300 nm.

5. The method of claim 1, wherein the steps of emitting light into the eye and detecting the remainder of the light reflected from the eye are performed using a combination light emission and detection device.

6. The method of claim 1, wherein the step of emitting light into the eye is performed using a light emission device and the step of detecting the remainder of the light reflected from the eye is performed using a light detection device separate from the light emission device.

* * * * *